United States Patent [19]

Mylari et al.

[11] Patent Number: 5,236,945
[45] Date of Patent: Aug. 17, 1993

US005236945A

[54] 1H-INDAZOLE-3-ACETIC ACIDS AS ALDOSE REDUCTASE INHIBITORS

[75] Inventors: Banavara L. Mylari, Waterford; William J. Zembrowski, Oakdale, both of Conn.

[73] Assignee: Pfizer Inc., New York, N.Y.

[21] Appl. No.: 776,533

[22] Filed: Oct. 11, 1991

Related U.S. Application Data

[63] Continuation of Ser. No. 499,279, Jun. 11, 1990, abandoned.

[51] Int. Cl.$^5$ ............................................. A61K 31/415
[52] U.S. Cl. ..................... 514/403; 514/322; 514/234.5; 514/866
[58] Field of Search ..................... 514/403, 234.5, 322, 514/866

[56] References Cited

U.S. PATENT DOCUMENTS 3,821,383 6/1974 Sestanj et al. ..................... 514/296
4,130,714 12/1978 Sarges ..................... 548/309

FOREIGN PATENT DOCUMENTS 8759 2/1980 European Pat. Off. .
49-035269 6/1974 Japan .
58-098060 8/1983 Japan .
58-144374 10/1983 Japan .

OTHER PUBLICATIONS

Pederson et al.—Abstract No. 321, 25th Meeting of the European Associates for the Study of Diabetes, Sep. 20-23, 1989.
Blohme and Smith—Abstract No. 47, 25th Annual Meeting of the European Associates for the Study of Diabetes, Sep. 20-23, 1989.
The Sorbinil Neuropathy Study Group—Abstract No. 55, *Diabetes* 38, May 1989.
Jaspan et al.—Abstract No. 56, *Diabetes* 38, May 1989.
Corsi et al., J. Med. Chem., vol. 19, pp. 778-783 (1976).
Wynganiden et al., Textbook of Medicine 16th edition, pp. 1061-1065, Nov. 1983.
Shibakawa et al., Current Chemotherapy and Infectious Disease, Proc. 11th ICC and 19th ICAAC, Am. Soc. of Microbiol., pp. 469-470, May 1980.

*Primary Examiner*—Jane T. Fan
*Attorney, Agent, or Firm*—Peter C. Richardson; Gregg C. Benson; Mervin E. Brokke

[57] ABSTRACT

Abstract Certain 1H-indazole-3-acetic acid derivatives, and their pharmaceutically-acceptable esters and salts, are inhibitors of the aldose reductase enzyme, and so are useful in the treatment of diabetic complications.

4 Claims, No Drawings

1H-INDAZOLE-3-ACETIC ACIDS AS ALDOSE REDUCTASE INHIBITORS

This is a continuation of application Ser. No. 07/499,279, filed on Jun. 11, 1990 now abandoned.

BACKGROUND OF THE INVENTION

The present invention is concerned with 1H-indazole-3-acetic acid derivatives and their pharmaceutically-acceptable esters and salts. By means of their inhibition of the aldose reductase enzyme, these compounds are useful in the treatment of diabetic complications.

Compounds, such as sorbinil (S-6-fluorospiro[chroman-4,4'-imidazoline]-2',5'-dione; Sarges, U.S. Pat. No. 4,130,714), which have aldose reductase inhibitory activity, are of value in controlling certain chronic complications arising from diabetes mellitus (e.g., diabetic cataracts and neuropathy).

Non-hydantoin compounds previously reported to inhibit aldose reductase include 1H-benz[d,e]isoquinoline-1,3(2H)-dione-2-acetic acid derivatives, Sestanj et al., U.S. Pat. No. 3,821,383; halogen substituted chroman-4-carboxylic and chroman-4-acetic acids, Belletire, U.S. Pat. No. 4,210,663; spiro[chroman-4,5'-oxazolidin]-2',3'-diones, Schnur, U.S. Pat. No. 4,200,642; and variously substituted phthalazin-1(2H)-on-4-acetic acids, Larson et al., published European Patent Application No. 222,576.

Variously substituted 1-benzyl-1H-indazole-3-carboxylic acids and specifically 1-(p-chlorobenzyl)-1H-3-acetic acid have been reported to be useful as antispermatogenic agents, Corsi et al., J. Med. Chem., vol 19, pp. 778-783 (1976).

SUMMARY OF THE INVENTION

The present invention is directed to compounds having the formula

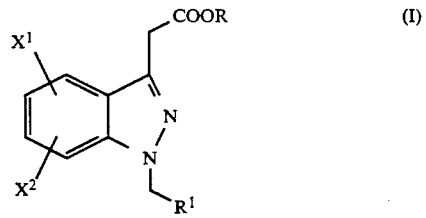

wherein
$X^1$ and $X^2$ are each independently hydrogen, fluoro, chloro, bromo, trifluoromethyl, $(C_1-C_3)$alkyl or $(C_1-C_3)$alkoxy;

R is hydrogen or a radical group forming a conventional ester which is hydrolyzable under physiological conditions;

$R^1$ is

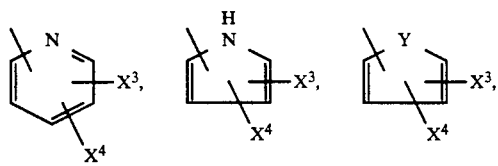

-continued

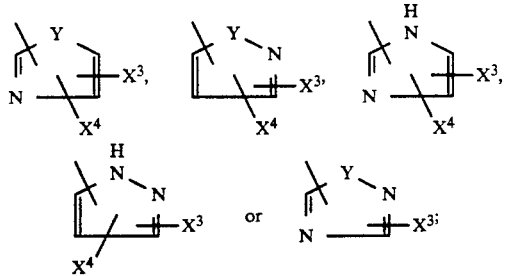

Y is sulfur or oxygen;
$X^3$, when taken separately, is hydrogen, fluoro, chloro, bromo, trifluoromethyl, $(C_1-C_3)$alkyl, $(C_1-C_3)$alkoxy or

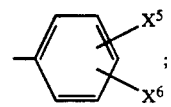

$X^4$, when taken separately, $X^5$ and $X^6$ are each independently hydrogen, fluoro, chloro, bromo, trifluoromethyl, $(C_1-C_3)$alkyl or $(C_1-C_3)$alkoxy; and $X^3$ and $X^4$, when taken together, are combined with the adjacent carbons to which they are attached to form a benzene ring substituted by $X^5$ and $X^6$;

the pharmaceutically acceptable cationic salts thereof when R is hydrogen; and the pharmaceutically acceptable acid addition salts thereof.

Esters of acidic pharmaceutical compounds (such as penicillins and non-steroidal antiinflammatory agents) which are hydrolyzed under physiological conditions (sometimes referred to as pro-drug esters) are becoming as common as pharmaceutically acceptable salts in the pharmaceutical art. Of particular value in the present instance are those esters wherein R is:
1H-furan-5-on-2-yl;
1H-isobenzofuran-2-on-7-yl;
gamma-butyrolacton-4-yl;
—$CH_2CH_2NR^2R^3$;
—$CHR^4OCOR^5$; or
—$CHR^4OCOOR^6$;
wherein
$R^2$ and $R^3$, taken separately, are each independently $(C_1-C_4)$alkyl; or taken together with the nitrogen to which they are attached form a pyrrolidine, piperidine or morpholine ring;
$R^4$ is hydrogen or methyl;
$R^5$ is $(C_1-C_6)$alkyl, $(C_1-C_6)$carboxyalkyl, carboxycyclohexyl or carboxyphenyl; and
$R^6$ is $(C_1-C_6)$alkyl.

The expression "pharmaceutically acceptable acid addition salt" refers to addition salts with inorganic and organic acids such as (but not limited to) HCl, HNO$_3$, H$_2$SO$_4$, H$_3$PO$_4$, CH$_3$SO$_3$H, CH$_3$C$_6$H$_4$SO$_3$H, CH$_3$COOH, fumaric acid, succinic acid and citric acid.

The expression "pharmaceutically acceptable cationic salt" refers to carboxylate salts where the cation is such as (but not limited to) sodium, potassium, calcium, magnesium, ammonium or protonated benzathine (N,N'-di-benzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

Because of their ease of preparation and valuable aldose reductase inhibitory activity, more preferred compounds of the formula (I) have $X^1$ as hydrogen or 5-chloro, $X^2$ as hydrogen, and R as

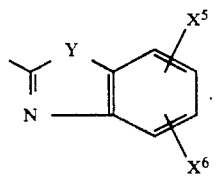

Most preferred compounds have Y as sulfur; and $X^1$ as 5-chloro, $X^5$ as hydrogen and $X^6$ as 5-fluoro; $X^1$, $X^5$ and $X^6$ each as hydrogen; $X^1$ as 5-chloro, $X^5$ as hydrogen and $X^6$ as 5-trifluoromethyl; $X^1$ as 5-chloro, $X^5$ as 5-fluoro and $X^6$ as 7-fluoro; or $X^1$ as hydrogen, $X^5$ as 5-fluoro and $X^6$ as 7-fluoro.

The present invention is also directed to pharmaceutical compositions for the control of chronic diabetic complications in mammals which comprise a compound of the formula (I) in a pharmaceutically acceptable carrier; and to a method of controlling chronic diabetic complications which comprises administering to a mammal suffering from chronic diabetes a chronic diabetic complication controlling amount of a compound of the formula (I).

A further subject of the present invention is a method of controlling chronic diabetic complications which comprises administering to a mammal suffering from chronic diabetes a chronic diabetic complication controlling amount of a compound of the formula

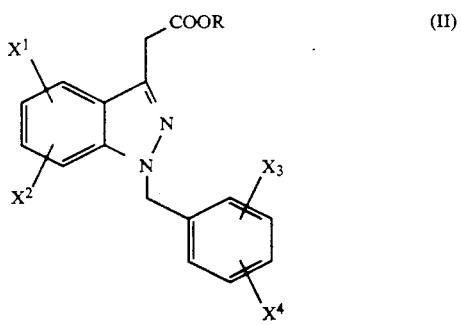

wherein R, $X^1$, $X^2$, $X^3$ and $X^4$ are as defined above.

DETAILED DESCRIPTION OF THE INVENTION

The aldose reductase inhibiting compounds (I) and (II) of the present invention are readily prepared according to the following scheme, in which R' is R (as defined above), $(C_1-C_4)$alkyl, phenyl or benzyl; R'' is $R^1$ or $-C_6H_3X^3X^4$ (both as defined above); and X is a leaving group susceptible to nucleophilic displacement:

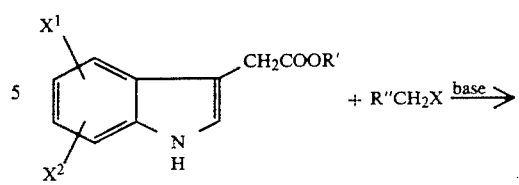

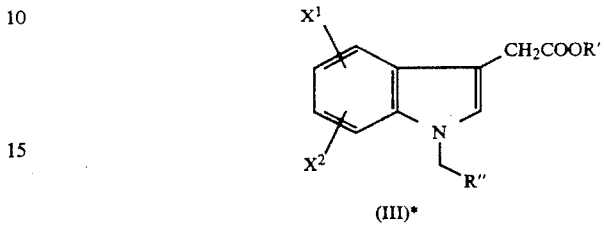

*(I) when R' is R and R'' is $R^1$
(II) when R' is R and R'' is $-C_6H_3X^3X^4$ when R' is H; conventional esterification when R' is $(C_1-C_4)$-alkyl, phenyl or benzyl; conventional hydrolysis (I) or (II) wherein R is a radical forming an ester hydrolyzable under physiological conditions (I) or (II) wherein R is H The displacement of X in the compound R''$CH_2X$ to form a compound of the formula (II) is a typical nucleophilic displacement reaction, generally carried out in a reaction inert solvent in the presence of a base. For example, the group X can be chloro, bromo, iodo, mesyl ($-SO_3CH_3$) or tosyl. For best results, the reaction is carried out on the anionic form of the 1H-indazole, readily obtained in situ by the action of a strong base on the free indazole. When R' is H, hydrous conditions are satisfactory, such that even KOH or NaOH are useful for this purpose. In this case, at least 2 molar equivalents (and usually an excess, e.g., 3-molar equivalents) of base are used, in order to form the dianion and assure selective reaction at nitrogen. However, when R is a radical forming an ester, anhydrous and (except when the solvent is R'OH) aprotic conditions are much preferred, so as to avoid undesired hydrolysis and/or ester exchange. Thus, in the latter case, sodium hydride (or where practical R'ONa) is the preferred base for prior formation of the anion. In this case, only one molar equivalent of the base is required, with no more than modest excesses (e.g., 0.1 molar equivalent) generally employed. Solvent is not critical in this nucleophilic displacement, except to generally avoid protic solvents other than R'OH (e.g., aqueous solvents are fully satisfactory when R' is H, methanolic solvents are satisfactory when R' is $CH_3$, etc.). In any case, the solvent should be significantly less acidic than the indazole so as to maintain the latter in anionic form. Temperature is likewise not critical, e.g., temperature ranges of about 0°-100° C. are generally satisfactory, temperatures at or near ambient being most convenient. For example, when X is bromo, the displacement will generally be complete within 15-30 minutes using a modest molar excess of the organic bromide to force the reaction to completion. Of course, when X is chloro, more time will be needed, while when X is iodo, less time will be needed. If desired, when X is other than iodo, the displacement reaction can be catalyzed by use of up to a mol or more of an iodide salt (e.g., NaI, KI).

As used here and elsewhere herein, the expression "reaction-inert solvent" refers to a solvent which does not interact with starting material, reagents, intermediates or desired product in a manner which adversely affects the yield of the desired product.

When R' corresponds to R as defined above, the desired product (I) or (II) is of course directly formed in the displacement reaction. On the other hand, when R' is ($C_1$-$C_4$)alkyl, phenyl or benzyl, the ester will then be conventionally hydrolyzed to form the compound of the formula (I) or (II) wherein R is hydrogen. Preferred are basic conditions, for example, using at least one molar equivalent (and usually an excess) of an aqueous alkali metal hydroxide, generally in the presence of a reaction-inert, water miscible organic solvent to aid in solubilizing the ester.

When in the product is (I) or (II) wherein R is hydrogen, and an ester hydrolyzable under physiological conditions is desired, such esters are also prepared according to usual methods. Thus when R is —$CH_2CH_2NR^2R^3$ the esters are readily prepared by reacting an activated form of the acid with a 2-(substituted-amino)ethanol of the formula

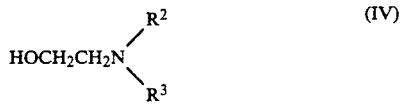

(IV)

Mixed anhydrides are well-suited as the activated form of the acid in such preparations. Generally, the acids are first converted in situ to a tertiary amine salt in the presence of a 1 to 1.1 molar excess of the amine. A variety of tertiary amines are suitable for this purpose. Exemplary are triethylamine, N-methylpiperidine, N-methylmorpholine, dimethylaniline or quinoline. Suitable inert solvents are methylene chloride, chloroform, dimethylformamide, and dimethylacetamide. It is preferrable that the acid be completely dissolved by the excess of tertiary amine, which may require a stirring period, together with gentle warming, if necessary. The solution of amine salt is then reacted with an equivalent of alkyl (e.g. ethyl), benzyl, or phenyl chloroformate, at a temperature in the range of —40° to 25° C., preferably in the range —10° to 10° C., to form a mixed anhydride in solution. Without isolation, the mixed anhydride is reacted directly with the appropriate alcohol of the formula (IV) to yield the desired ester. The reaction is usually initiated at a cool temperature (such as —40° to 15° C.), but allowed to warm to higher temperature (such as 15° to 40° C.) to complete the reaction. Alternatively, such esters are prepared by ester exchange, as specifically exemplified below. Thus, an intermediate ester of the formula (III) wherein R' is ($C_1$-$C_4$)alkyl, phenyl or benzyl is reacted with an excess of the sodium salt of the amino alcohol (IV). The latter is generally formed in situ by reaction of the amino alcohol with NaH, in a reaction-inert solvent such as toluene, usually at a temperature in the range of 15°-85° C.

The esters wherein R is a conventional radical forming an ester which is hydrolyzable under physiological conditions are more generally prepared by reaction of a salt of the acid (I or II, R=H; preferably the tetrabutylammonium salt) with an appropriate compound containing a displaceable halide (iodide, bromide or chloride; generally preferred, where available, in that order), or another group suitable for nucleophilic displacement. Exemplary are $CH_3OSO_2CH_3$, $C_2H_5Br$, $CH_3CH_2CH_2I$, $ICHR^4OCOR^5$, $ICHR^4OCOOR^6$,

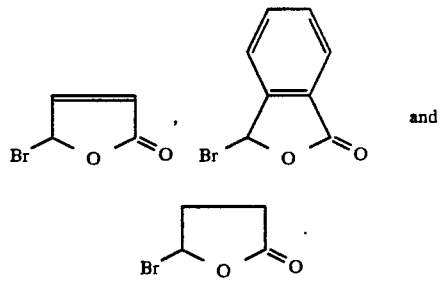

The required salt can be in isolated form, or more conveniently, formed in situ from the acid by use of at least one equivalent of a base. The reaction is carried out in a reaction-inert solvent, preferably one which is essentially anhydrous. A particularly convenient reaction system employs excess potassium carbonate as base in acetone as solvent. When the halide is chloro or bromo, up to three or more equivalents of anhydrous sodium iodide is added, if desired, to enhance the rate of reaction. An excess of the halide reagent is not critical to the reaction, but such an excess will generally be used in order to force the reaction to completion in a shorter period of time. The rate of reaction will also depend greatly on the halide (e.g., I>Br>Cl) and on the nature of the radical group R (e.g., more branched $ICHC-H_3OCOCH_3$ will react more slowly than $ICH_2OCOCH_3$). The reaction temperature is not critical, a temperature in the range of 0°-100° C. being generally satisfactory, but ambient or near ambient temperatures are preferred. Another preferred method converts the free acid form into the tetrabutylammonium salt, formed in water and extracted into an organic solvent such as chloroform, which is then reacted with the organic halide. A typical procedure employing the latter method is exemplified below.

By conventional modification of the isolation procedure, the compounds of the formula (I) and (II) are alternatively isolated in the form of a pharmaceutically-acceptable acid addition salt, as defined above. Such salts are also readily prepared from the isolated free base forms by standard methods. For example, a molar equivalent of HCl, HBr, $HNO_3$ or succinic acid, or a half a molar equivalent of $H_2SO_4$ or succinic acid is combined with the free base in an organic or aqueous solvent to form the HCl, HBr, $HNO_3$, hemisuccinate, bisulfate or succinate salt, respectively. The salt is isolated by concentration and/or the addition of a non-solvent.

Similarly, by modification of the isolation procedure, the compounds of the formula (I) or (II) wherein R is H are alternatively isolated in the form of a pharmaceutically-acceptable cationic salt, as defined above. Such salts are also readily prepared from the isolated acid forms by standard methods. For example, an equivalent of the corresponding cationic hydroxide, carbonate or bicarbonate, or of an amine, is combined with the carboxylic acid in an organic or aqueous solvent. The salt is isolated by concentration and/or the addition of a non-solvent.

The 1H-indazole-3-acetic acids generally required as starting materials for synthesis of the compounds of the present invention are readily available according to literature methods, for example, by chain extension of an extensive variety of 1H-indazole-3-carboxylic acids described in above cited Corsi et al., using the method also there described:

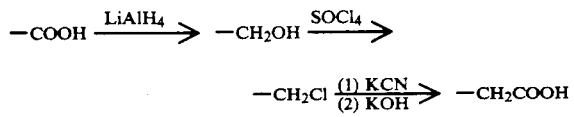

Corresponding ($C_1$–$C_4$)alkyl, benzyl or phenyl 1H-indazole-3-acetate esters are best prepared by conventional acid catalyzed esterification, as exemplified in the preparations below. The same can be applied to the preparation of 1H-indazole-3-acetate esters of aminoethanols of the formula (IV), which are alternatively prepared by the ester exchange method exemplified below. It will be evident to those skilled in the art that any such esters which are prepared via activated forms of the acid, or via nucleophilic displacement will generally require protection of the indazole nitrogen, e.g., by means of a benzyloxycarbonyl group removable by hydrogenolysis once the ester group is in place. As a practical matter, it is therefore usually preferred to introduce such ester groups after the benzyl or heteroarylmethyl group is already in place.

Variously substituted benzyl halides and heteroarylmethyl halides also required as starting materials are also readily available, in many cases commercially, but in any event by conventional methods, for example, from corresponding carboxylate esters, carboxylic acids, aldehydes, and carbinols, e.g.

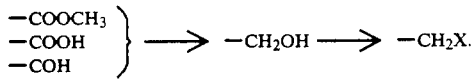

The present compounds of the formulas (I) and (II), particularly in their acid or salt form, are tested in vitro for their ability to reduce or inhibit aldose reductase enzyme activity, following the procedure described in U.S. Pat. No. 3,821,383 and based on the procedure of Hayman et al., Journal of Biological Chemistry, 240, 877 (1965). The substrate employed is partially purified aldose reductase enzyme obtained from human placenta. The results obtained with each compound at a concentration of $10^{-5}$M or lower are expressed as percent inhibition of enzyme activity, or, when tested at several concentration levels, expressed as an $IC_{50}$, the inhibition concentration calculated to show 50% inhibition of enzyme activity.

The present compounds of the formulas (I) and (II) are tested in vivo for their ability to reduce or inhibit sorbitol accumulation in the sciatic nerve of streptozotocinized (i.e., diabetic) rats by a procedure essentially as described in U.S. Pat. No. 3,821,383. In the present study, the amount of sorbitol accumulation in the sciatic nerves was measured 27 hours after induction of diabetes. The compounds are generally administered orally at doses ranging from 2.5 to 100 mg/kg at 4, 8 and 24 hours following the administration of streptozotocin. The results obtained in this manner are presented in terms of percent inhibition afforded by the test compound as compared to the case where no compound was administered (i.e., the untreated animal where sorbitol levels normally rise from approximately 50–100 mM/g tissue to as high as 400 mM/g tissue during the test period). In this test values below 20% are not always experimentally and statistically significant. Not all of the compounds of the present invention show in vivo activity by this oral test. Such compounds will find parenteral or topical use as described below.

The compounds of this invention are all readily adapted to therapeutic use as aldose reductase inhibitors for the control of chronic diabetic complications in mammals. They are administered either orally or parenterally, or topically as eye drops, in dosages ranging from about 0.1 to 10 mg/kg of body weight per day in single or divided doses. Of course, in particular situations, at the discretion of the attending physician, doses outside of this range will be used.

The compounds of this invention can be administered in a wide variety of different dosage forms, i.e., they may be combined with various pharmaceutically-acceptable inert carriers in the form of tablets, capsules, lozenges, troches, hard candies, powders, sprays, elixirs, syrups, injectable or eye drop solutions, and the like. Such carriers include solid diluents or fillers, sterile aqueous media and various non-toxic organic solvents.

For purposes of oral administration, tablets containing various excipients such as sodium citrate, calcium carbonate and calcium phosphate are employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the essential active ingredient therein can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble, alkali metal or alkaline-earth metal salts previously enumerated. Such aqueous solutions should be suitably buffered, if necessary, and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of topical administration, dilute, sterile, aqueous solutions (usually in about 0.1% to 5% concentration), otherwise similar to the above parenteral solutions, are prepared in containers suitable for dropwise administration to the eye.

The present invention is illustrated by the following examples. However, it should be understood that the invention is not limited to the specific details of these examples.

EXAMPLE 1

1-[(benzothiazol-2-yl)methyl]-1H-indazole-3-acetic acid

To a vigorously stirring solution of 1H-indazole-3-acetic acid (0.88 g) in water (100 ml) containing sodium hydroxide (0.60 g) was added 2-(bromomethyl)benzothiazole (1.25 g) and the resulting mixture heated at 80° C. for 2.5 hours. The reaction solution was cooled to room temperature and extracted with ether (2×25 ml). The aqueous layer was collected and acidified to a pH of about 4.0 with concentrated HCl, and then extracted with ethyl acetate (2×20 ml). The organic layers were combined, dried and evaporated to a yellow solid (yield: 0.67 g), which was crystallized from benzene (m.p. 164°–165° C.).

Substituting a molar equivalent of 5-chloro-1H-indazole-3-acetic acid for 1H-indazole-3-acetic acid, the same method was employed to prepare:

1-(benzothiazol-2-yl)methyl-5-chloro-1H-indazole-3-acetic acid (m.p. 213° C.).

Further substituting a molar equivalent of 2-(bromomethyl)benzo[d]isothiazole, 2-(bromomethyl)benzoxazole or 2-bromomethylquinoline for the 2-(bromomethyl)benzothiazole, the same method was used to prepare:

1-[(benzo[d]isothiazol-3-yl)methyl]-5-chloro-1H-indazole-3-acetic acid (m.p. 204°–205° C.);

1-[(benzoxazol-2-yl)methyl]-5-chloro-1H-indazole-3-acetic acid (m.p. 194°–195° C.); and 1-[(2-quinolyl)methyl]-5-chloro-1H-indazole-3-acetic acid (m.p. 201°–202° C.).

EXAMPLE 2

Methyl 1-(4-bromo-2-fluorobenzyl)-1H-indazole-3-acetate

To a solution obtained by adding sodium hydride (0.14 g; 50% w/w dispersion in mineral oil) to dimethylformamide (3 ml) containing methyl 1H-indazole-3-acetate (0.45 g) was added 4-bromo-2-fluorobenzyl bromide (0.70 g). After 15 minutes, the reaction solution was poured onto ice water (20 ml). Sufficient 10% HCl was added to adjust the pH to about 4.0 and the solution then extracted with ethyl acetate (2×20 ml). The combined organic extract was washed with water (2×20 ml), dried and evaporated. The residue was purified by chromatography on silica gel [yield: 0.31 g; $^1$H NMR (CDCl$_3$) 3.6 (s, 3H), 4.0 (s, 2H), 5.4 (s, 2H) 6.8–7.2 (m, 6H), 7.6 (m, 1H)].

Substituting a molar equivalent of 2-(bromomethyl)-5-(trifluoromethyl)benzothiazole, 2-(bromomethyl)-5-fluorobenzothiazole, 2-(bromomethyl)benzothiophene, 2-(bromomethyl)-5-(trifluoromethyl)benzoxazole or 2-(bromomethyl)-5,7-difluorobenzthiazole, respectively for 4-bromo-2-fluorobenzyl bromide, the same method was used to prepare:

methyl 1-[(5-(trifluoromethyl)benzothiazol-2-yl)methyl]-1H-indazole-3-acetate [$^1$H NMR (CDCl$_3$, 60 MHz): 3.65 (s, 3H), 4.0 (s, 2H), 5.9 (s, 2H), 7.0–8.2 (m, 7H)];

methyl 1-[(5-fluorobenzthiazol-2-yl)methyl]-1H-indazole-3-acetate [$^1$H NMR (CDCl$_3$, 60 MHz): 3.6 (s, 3H), 4.05 (s, 2H), 5.9 (s, 2H), 6.9–7.9 (m, 7H)];

methyl 1-[(benzothien-2-yl)methyl]-1H-indazole-3-acetate [$^1$H NMR (CDCl$_3$, 60 MHz): 3.65 (s, 3H), 4.05 (s, 2H), 4.65 (s, 2H), 7.0–7.8 (m, 9H)];

methyl 1-[(5-(trifluoromethyl)benzoxazol-2-yl)methyl]-1H-indazole-3-acetate [$^1$HNMR (CDCl$_3$, 60 MHz); 3.50 (s, 3H), 4.05 (s, 2H), 4.8 (s, 2H), 7.0–7.9 (m, 7H)]; and methyl 1-[(5,7-difluorobenzothiazol-2-yl)methyl]-1H-indazole-3-acetate [$^1$HNMR (CDCl$_3$, 60 MHz);; 1.3 (t, J=8 Hz, 3H), 4.0 (s, 2H), 4.15 (q, J=8 Hz, 2H), 5.9 (s, 2H), 6.9 (m, 1H), 7.2–7.7 (m, 5H).

Further substituting a molar equivalent of the corresponding ethyl ester for methyl 1H-indazole-3-acetate, and a molar equivalent of 2-(bromomethyl)-6-bromobenzothiazole, 2-(bromomethyl)-5-chlorobenzoxazole or 5-(bromomethyl)-3-(2-bromophenyl)-1,2,4-oxadiazole, respectively, for 4-bromo-2-fluorobenzyl bromide, the same method was used to prepare:

ethyl 1-[(6-bromobenzothiazol-2-yl)methyl]-1H-indazole-3-acetate [$^1$HNMR CDCl$_3$, 60 MHz): 1.25 (t, J=8 Hz, 3H), 4.05 (s, 2H), 4.2 (q, J=8 Hz, 2H), 5.9 (s, 2H), 7.1–7.9 (m, 7H)];

ethyl 1-[(5-chlorobenzoxazol-2-yl)methyl]-1H-indazole-3-acetate [$^1$HNMR (CDCl$_3$, 60 MHz): 11.2 (t, J=8 Hz, 3H), 4.0 (s, 2H), 4.1 (q, J=8 Hz, 2H), 5.8 (s, 2H), 7.0–7.8 (m, 7H)]; and ethyl 1-[(3-(2-bromophenyl)-1,2,4-oxadiiazol-5-yl)methyl]-1H-indazole-3-acetate [$^1$HNMR (CDCCl$_3$, 60 MHz): 1.2 (t, J=8 Hz, 3H), 4.0 (s, 2H), 4.2 (q, J=8 Hz, 2H), 5.8 (s, 2H), 7.1–7.7 (m, 8H)].

Further substituting a molar equivalent of ethyl 5-chloro-1H-indazole-3-acetate for the methyl 1H-indazole-3-acetate, and 2-(bromomethyl)-5-bromobenzothiazole, 2-(bromomethyl)-5-chlorobenzoxazole, 2-(bromomethyl)-5-fluorobenzothiazole and 2-(bromomethyl)-5-(trifluoromethyl)benzothiazole, respectively, for the 4-bromo-2-fluorobenzyl bromide, the same method was used to prepare:

ethyl 1-[(5-bromobenzothiazol-2-yl)methyl]-5-chloro-1H-indazole-3-acetate. $^1$HNMR (CDCl$_3$, 60 MHz): 1.30 (t, J=8 Hz, 3H), 4.0 (s, 2H), 4.2 (q, J=8 Hz, 2H), 5.85 (s, 2H), 7.1 (m, 4H), 7.6 (dd, J=2,7 Hz, 1H), 8.05 (d, J=2 Hz, 1H)];

ethyl 1-[(5-chlorobenzoxazol-2-yl)methyl-5-chloro-1H-indazole-3-acetate [$^1$HNMR (CDCl$_3$, 60 MHz): 1.25 (t, J=8 Hz, 3H), 3.95 (s, 2H), 4.1 (q, J=8 Hz, 2H), 5.65 (s, 2H), 7.1 (m, 5H), 7.5 (m, 2H)];

ethyl 1-[(5-fluorobenzthiazol-2-yl)methyl-5-chloro-1H-indazole-3-acetate [$^1$HNMR (CDCl$_3$, 60 MHz): 1.3 (t, J=8 Hz, 3H), 4.1 (s, 2H), 4.2 (q, J=8 Hz, 2H), 5.95 (s, 2H), 7.1–7.9 (m, 6H)]; and ethyl 1-[(5-trifluoromethyl)benzothiazol-2-yl)methyl]-5-chloro-1H-indazole-3-acetate [$^1$HNMR (CDCl$_3$, 60 MHz): 1.25 (t, J=8 Hz, 3H), 4.05 (s, 2H), 4.2 (q, J=8 Hz, 2H), 5.9 (s, 2H), 7.1–8.2 (m, 6H)].

Further substituting a molar equivalent of methyl 5-chloro-1H-indazole-3-acetate for the methyl 1H-indazole-3-acetate, and 2-(bromomethyl)-5,7-difluorobenzothiazole for the 4-bromo-2-fluorobenzyl bromide, the same method was used to prepare:

methyl 5-chloro-1-[(5,7-difluorobenzothiazol-2-yl)methyl]-1H-indazole-3-acetate [m.p. 109°–112° C.].

EXAMPLE 3

1-(4-bromo-2-fluorobenzyl)-1H-indazole-3-acetic acid

A solution of methyl 1-(4-bromo-2-fluorobenzyl)-1H-indazole-3-acetate (0.30 g) in methanol (5 ml) containing 10% aqueous KOH (1 ml) was stirred at room temperature for 16 hours. It was then concentrated to a low volume, and then diluted with ethyl acetate (10 ml) and sufficient 10% HCl added to adjust the pH to about 4.0. The ethyl acetate layer was washed with water (5 ml), dried and then evaporated to a white solid (yield: 0.21 g; m.p. 167°-168° C.).

By the same method, the other methyl and ethyl esters of the proceding Example were converted to:

1-[(5-(trifluoromethyl)benzothiazol-2-yl)methyl]-[1H-indazole-3-acetic acid (m.p. 168°-169° C.);

1-[(5-fluorobenzothiazol-2-yl)methyl]1H-indazole-3-acetic acid (m.p. 173°-174° C.);

1-[(benzothien-2-yl)methyl]-1H-indazole-3-acetic acid (m.p. 164°-165° C.);

1-[(5-(trifluoromethyl)benzoxazol-2-yl)methyl]-1H-indazole-3-acetic acid (m.p. 204°-205° C.);

1-[(5,7-difluorobenzothiazol-2-yl)methyl]-1H-indazole-3-acetic acid (m.p. 168°-169° C.);

1-[(6-bromobenzothiazol-2-yl}methyl]-1H-indazole-3-acetic acid (m.p. 186°-189° C.);

1-[(5-chlorobenzoxazol-2-yl)methyl]-1H-indazole-3-acetic acid (m.p. 197°-198° C.);

1-[(3-(2-bromophenyl)-1,2,4-oxadiazol-5-yl)methyl]-1H-indazole-3-acetic acid (m.p. 208°-209° C.);

1-[(5-bromobenzothiazol-2-yl)methyl]-5-chloro-1H-indazole-3-acetic acid (m.p. 210°-211° C.);

1-[(5-chlorobenzoxazol-2-yl)methyl-5-chloro-1H-indazole-3-acetic acid (m.p. 227°-228° C.);

1-[(5-fluorobenzothiazol-2-yl)methyl-5-chloro-1H-indazole-3-acetic acid (m.p. 186°-188° C.); and 1-[(5-(trifluoromethyl)benzothiazol-2-yl)methyl-]5-chloro-1H-indazole-3-acetic acid (m.p. 189°-190° C.);

1-[(5,7-difluorobenzothiazol-2-yl)methyl]-5-chloro-1H-indazole-3-acetic acid (m.p. 196° C.).

EXAMPLE 4

By the methods of the preceding Examples 1-3, the following additional compounds are prepared from a suitably substituted 1H-indazole-3-acetic acid, or methyl or ethyl ester thereof, and a suitably substituted benzyl or (heteroaryl)methyl halide:

1-[(3-pyridyl)methyl]-1H-indazole-3-acetic acid;

1-[(4-methyl-2-pyridyl)methyl]-1H-indazole-3-acetic acid;

1-[(2-pyrrolyl)methyl]-5-methoxy-1H-indazole-3-acetic acid;

1-[(5-benzothiazolyl)methyl]-5-methyl-1H-indazole-3-acetic acid;

1-[(5-benzothiazolyl)methyl]-5-methoxy-1H-indazole-3-acetic acid;

1-(4-fluorobenzyl)-1H-indazole-3-acetic acid;

1-(3-methoxybenzyl)-1H-indazole-3-acetic acid;

1-(2,4-dimethylbenzyl)-1H-indazole-3-acetic acid;

1-[(1-isoquinolyl)methyl]-1H-indazole-3-acetic acid;

1-(2-thenyl)-1H-indazole-3-acetic acid;

1-furfuryl-1H-indazole-3-acetic acid;

1-[(4-thiazolyl)methyl]-1H-indazole-3-acetic acid;

1-[(3-isoxazolyl)methyl]-1H-indazole-3-acetic acid;

1-[(1-isoindolyl)methyl]-1H-indazole-3-acetic acid;

1-[(2-indolyl)methyl-1H-indazole-3-acetic acid;

1-[(3(1H)-indazolyl)methyl]-1H-indazole-3-acetic acid;

1-[(2-imidazolyl)methyl]-1H-indazole-3-acetic acid;

1-[(1,2,4-thiadiazol-5-yl)methyl]-5-chloro-1H-indazole-3-acetic acid.

EXAMPLE 5

Pivaloyloxymethyl
1-[(5-(Trifluoromethyl)benzothiazol-2-yl)methyl]-5-chloro-1H-indazole-3-acetate Tetrabutylammonium hydrogen sulfate (0.374 g, 1.1 mmol) is dissolved in 2.5 ml H₂O. NaHCO₃(92 mg, 1.1 mmol) is added portionwise at a rate which controls the foaming. Finally, 1-[(5-trifluoromethyl)benzothiazol-2-yl)methyl]-5-chloro-1H-indazole-3-acetic acid (1.1 mmol) is added. After about 30 minutes of stirring, the solution is extracted 4×5 ml CHCl₃ and the combined extracts are dried and stripped to yield the intermediate tetrabutylammonium salt. Under nitrogen, the latter is dissolved in 2 ml acetone and chloromethyl pivalate (0.216 ml, 1.1 mmol) is added. After 24 hours, the acetone is stripped and the residue dissolved in 5 ml ethyl acetate, washed 3×5 ml water and 1×5 ml brine, dried and restripped to yield title product, which, if desired, is further purified by chromatography on silica gel.

By the same method, substituting a molar equivalent of the appropriate organic halide for chloromethyl pivalate, the following additional esters are prepared:

furan-5(1H)-on-1-yl 1-[(5-(trifluoromethyl)-benzothiazol-2-yl)methyl]-5-chloro-1H-indazole-3-acetate;

isobenzofuran-3(1H)-on-1-yl 1-[(5-trifluoromethyl)-benzothiazol-2-yl)methyl]-5-chloro-1H-indazole-3-acetate;

gamma-butyrolacton-4-yl 1-[(5-trifluoromethyl)benzothiazol-2-yl)methyl]-5-chloro-1H-indazole-3-acetate;

1-(ethoxycarbonyloxy)ethyl 1-[(5-trifluoromethyl)-benzothiazol-2-yl)methyl]-5-chloro-1H-indazole-3-acetate.

EXAMPLE 6

2-Morpholinoethyl
1-[(5-Bromobenzothiazol-2-yl)methyl]-5-chloro-1H-indazole-3-acetate Hydrochloride To the sodium salt of N-(2-hydroxyethyl)morpholine, prepared by cautiously adding sodium hydride (0.45 g; 50% w/w dispersion in mineral oil) to a solution of N-(2-hydroxyethyl)morpholine (1.43 ml) in toluene (50 ml), is added a solution of ethyl 1-[(5-bromobenzothiazol-2-yl)methyl-5-chloro-1H-indazole-3-acetate (1.23 g) in toluene (30 ml). After stirring at room temperature for 24 hours and then at 60° C. for 6 hours, the reaction mixture is saturated with dry HCl gas. The precipitated solids are recovered by filtration, added to saturated aqueous sodium bicarbonate (100 ml), and extracted with ethyl acetate (3×100 ml). The organic layer is dried, evaporated and the resulting residue dissolved in acetone (30 ml). Saturation of this solution with dry HCl yields the title compound.

EXAMPLE 7

2-(Morpholino)ethyl
1-(4-bromo-2-fluorobenzyl)-1H-3-acetate

Substituting the title product of Preparation 2 for the methyl 1H-indazole-3-acetate, the method of Example 2 is used to prepare present title product.

PREPARATION 1

Methyl 1H-indazole-3-acetate A solution of 1H-indazole-3-acetic acid (1.0 g) in methanol (30 ml) containing five drops of concentrated sulfuric acid was refluxed for 8 hours. It was then concentrated to a low volume, diluted with ethyl acetate (20 ml). The organic layer washed with water (2×10 ml) and then with sodium bicarbonate solution (10 ml, 10%). The ethyl acetate layer was collected and then dried to obtain the title compound (yield: 0.8 g; m.p. 146° C.).

The corresponding ethyl ester was prepared by substituting anhydrous ethanol for methanol.

PREPARATION 2

2-(Morpholino)ethyl 1H-Indazole-3-acetate

By the method of Example 6, the title product of the preceding Example is converted to present title product.

We claim:

1. A method of controlling chronic diabetic complications which comprises administering to a mammal suffering from chronic diabetes a chronic diabetic complication controlling amount of a compound of the formula

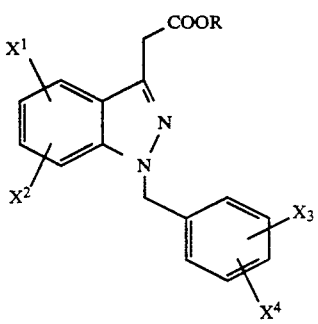

wherein $X^1$ and $X^2$ are each independently hydrogen, fluoro, chloro, bromo, trifluoromethyl, $(C_1-C_3)$alkyl or $(C_1-C_3)$alkoxy;

R is hydrogen or a racial group forming a conventional ester which is hydrolyzable under physiological conditions;

$X^3$, when taken separately, is hydrogen, fluoro, chloro, bromo, trifluoromethyl, $(C_1-C_3)$alkyl, $(C_1-C_3)$alkoxy or

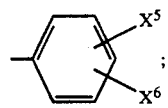
;

$X^4$, when taken separately, $X^5$ and $X^6$ are each independently hydrogen, fluoro, chloro, bromo, trifluoromethyl, $(C_1-C_3)$alkyl or $(C_1-C_3)$alkoxy; and $X^3$ and $X^4$, when taken together, are combined with the adjacent carbons to which they are attached to form a benzene ring substituted by $X^5$ and $X^6$;

a pharmaceutically acceptable cationic salt thereof when R is hydrogen; or a pharmaceutically acceptable acid addition salt thereof.

2. A method of claim 1 wherein R is:
1H-furan-5-on-2-yl;
1H-isobenzofuran-2-on-7-yl;
gamma-butyrolacton-4-yl;
—$CH_2CH_2NR^2R^3$;
—$CHR^4OCOR^5$; or —$CHR^4OCOOR^6$; wherein $R^2$ and $R^3$, taken separately, are each independently $(C_1-C_4)$alkyl; or taken together with the nitrogen to which they are attached form a pyrrolidine, piperidine or morpholine ring;

$R^4$ is hydrogen or methyl;

$R^5$ is $(C_1C_6)$alkyl, $(C_{1-6})$carboxyalkyl, carboxycyclohexyl or carboxyphenyl; and $R^6$ is $(C_1-C_6)$alkyl.

3. A method of claim 1 wherein R is hydrogen.

4. The method of claim 3 wherein $X^1$ and $X^2$ are each hydrogen, $X^3$ is 2-fluoro and $X^4$ is 4-bromo.

* * * * *